(12) United States Patent
Schuler et al.

(10) Patent No.: US 8,071,089 B2
(45) Date of Patent: Dec. 6, 2011

(54) COMPOSITION WITH A FUNGAL (YEAST) LIPASE AND METHOD FOR TREATING LIPID MALABSORPTION IN CYSTIC FIBROSIS AS WELL AS PEOPLE SUFFERING FROM PANCREATIC LIPASE INSUFFICIENCY

(75) Inventors: Christopher Schuler, Charlottesville, VA (US); Edward Schuler, Keswick, VA (US)

(73) Assignee: BIO-Cat, Inc., Troy, VA (US)

( * ) Notice: Subject to any disclaimer, the term of this patent is extended or adjusted under 35 U.S.C. 154(b) by 302 days.

(21) Appl. No.: 12/092,255

(22) PCT Filed: Oct. 31, 2006

(86) PCT No.: PCT/US2006/042466
§ 371 (c)(1),
(2), (4) Date: Apr. 30, 2008

(87) PCT Pub. No.: WO2007/053619
PCT Pub. Date: May 10, 2007

(65) Prior Publication Data
US 2008/0279839 A1    Nov. 13, 2008

Related U.S. Application Data

(60) Provisional application No. 60/731,813, filed on Nov. 1, 2005.

(51) Int. Cl.
*A61K 38/54* (2006.01)
(52) U.S. Cl. .................... 424/94.6; 424/94.2; 424/94.63; 424/94.66
(58) Field of Classification Search .................. None
See application file for complete search history.

(56) References Cited

U.S. PATENT DOCUMENTS

| | | | |
|---|---|---|---|
| 4,079,125 A | 3/1978 | Sipos | |
| 4,447,412 A * | 5/1984 | Bilton | 424/498 |
| 4,826,679 A | 5/1989 | Roy | |
| 4,944,944 A | 7/1990 | Tang et al. | |
| 5,234,697 A | 8/1993 | Sipos | |
| 5,260,074 A | 11/1993 | Sipos | |
| 5,302,400 A | 4/1994 | Sipos | |
| 5,324,514 A * | 6/1994 | Sipos | 424/94.63 |
| 5,352,460 A | 10/1994 | Sipos | |
| 5,387,422 A * | 2/1995 | Handel et al. | 426/2 |
| 5,405,621 A | 4/1995 | Sipos | |
| 5,415,872 A | 5/1995 | Sipos | |
| 5,460,812 A | 10/1995 | Sipos | |
| 5,489,530 A | 2/1996 | Braatz et al. | |
| 5,569,458 A | 10/1996 | Greenberg | |
| 5,578,304 A | 11/1996 | Sipos | |
| 5,614,189 A | 3/1997 | Huge-Jensen | |
| 5,645,832 A | 7/1997 | Braatz et al. | |
| 5,750,104 A | 5/1998 | Sipos | |
| 5,827,718 A | 10/1998 | Ishida et al. | |
| 6,030,798 A | 2/2000 | Braatz et al. | |
| 6,051,220 A * | 4/2000 | Scharpe | 424/94.2 |
| 6,534,303 B2 | 3/2003 | Mahadik et al. | |
| 6,676,933 B2 | 1/2004 | Vergez et al. | |
| 2001/0046493 A1 | 11/2001 | Margolin et al. | |
| 2002/0018773 A1 | 2/2002 | Kondo | |
| 2002/0061302 A1 | 5/2002 | Sander-Struckmeier et al. | |
| 2003/0007962 A1 | 1/2003 | Vergez et al. | |
| 2003/0017144 A1 | 1/2003 | Margolin et al. | |
| 2003/0129218 A1 | 7/2003 | Smoler | |
| 2003/0157087 A1 | 8/2003 | Berna et al. | |
| 2003/0215438 A1 | 11/2003 | Hausch et al. | |
| 2004/0033220 A1 | 2/2004 | Hartmann | |
| 2004/0057944 A1 | 3/2004 | Galle et al. | |
| 2006/0121017 A1 | 6/2006 | Margolin et al. | |
| 2006/0128587 A1 | 6/2006 | Margolin et al. | |

FOREIGN PATENT DOCUMENTS

| | | |
|---|---|---|
| EP | 0 238 023 | 9/1987 |
| EP | 0 387 945 | 3/1990 |
| EP | 0489718 | 10/1992 |
| WO | WO 85/03438 | 8/1985 |
| WO | WO 89/01969 | 3/1989 |
| WO | WO 91/18623 | 12/1991 |
| WO | WO 01/72783 | 10/2001 |
| WO | WO 2006/044529 | 4/2006 |

OTHER PUBLICATIONS

Griffin et al., Gut, 1989, vol. 30, p. 1012-1015.*
Beverley et al., Archives of Disease in Childhood, 1987, vol. 62, p. 564-568.*
Cichoke, A. J., The Complete Book of Enzyme Therapy, 1999, pp. 48 and 49.*
Patel et al., Journal of Food Science, 1996, vol. 61, No. 1, p. 33-38, and 73.*
Tanaka et al., JAOCS, 1992, vol. 69, No. 12, p. 1210-1214.*
Pandey, et al., "Biotechnology and Applied Biochemistry", Medline/PubMed Citation, vol. 31, pp. 135-152, (2000).
Shintani, et al., "Engineering of Porcine Pepsin. Alteration of S1 Substrate Specificity of Pepsin to Those of Fungal Aspartic Proteinases by Sit Directed Mutagenesis", Entrez PubMed, J. Biol. Chem. vol. 272, No. 30, pp. 18855-18861 (1997).
Takahashi, et al., "Independent Production of Two Molecular Forms of a Recombination of *Rhizopus oryzae* Lipase by KEX2-Engineered Strains of *Saccharaomyces cerevisiae*", Entrez PubMed, Appl. Microbiol Biotechnol. vol. 52, No. 4, pp. 534-540, (Oct. 1999).
Zandonella, "Interactions of Fluorescent Triacylglycerol Analogs Covalently Bound to the Active Site of a Lipase from *Rhizopus oryzae*", European Journal Biochemistry, vol. 262, pp. 63-69, (1999).
Akeboshi, et al., "Insights into the Reaction Mechanism of Glycosyl Hydrolase Family 49", European Journal of Biochemistry, vol. 271, issue 22, p. 4420, (Nov. 2004).

(Continued)

*Primary Examiner* — Kade Ariani
(74) *Attorney, Agent, or Firm* — Hunton & Williams LLP

(57) ABSTRACT

The invention provides compositions and methods for treating pancreatic enzyme insufficiency, such as the pancreatic enzyme insufficiency associated with cystic fibrosis. The invention also provides compositions comprising lipase from *Candida cylindracea*, alone or in combination with amylase or amyloglucosidase, protease and/or lactase. Furthermore, the invention discloses methods for treating pancreatic enzyme insufficiency comprising administering compositions to patients in need thereof.

22 Claims, 9 Drawing Sheets

OTHER PUBLICATIONS

Svendsen, "Review: Lipase Protein Engineering", Elsevier, Biochemica et Biophysica Acta, vol. 1543, pp. 223-238, (2000).

Yadav, et al., "Purification and Characterization of a Regiospecific Lipase from *Aspergillus terreus*", Biotechnol. Appl. Biochem., vol. 28, pp. 243-249, (1998).

Jorger, et al., "Alteration of Chain Length Selectivity of a *Rhizopus delemar* Lipase Through Site-Directed Mutagenesis", PubMed, AU-KBC Research Centre, Lipids, vol. 29, No. 6, p. 377-384, Jun. 29, 1994).

Chang, et al., "Purification and Properties of Alpha-Amylase from *Aspergillus oryzae* ATCC 76080", PubMed, Biochem. Mol. Biol. Int., vol. 36, No. 1, pp. 185-193, (May 1995).

Pazur, et al., "Comparison of the Properties of Glucoamylases from *Rizopus niveus* and *Aspergillus niger*", Biotechnology and Applied Biochemistry, vol. 12, pp. 63-78 (1990).

Graham, "Enzyme Replacement Therapy of Exocerine Pancreatic Insufficiency in Man", New England Journal of Medicine, vol. 296, pp. 1314-1317, (Jun. 9, 1977).

Wolfe, et al., "Pancreatic Enzymes", Retrieved from the Internet at: http://www.cysticfibrosismedicine.com/htmldocs/CFText/enzymes.htm, (Jan. 2001).

Layer, "Lipase Supplementation Therapy: Standards, Alternatives, and Perspectives", Entrez PubMed, LWWOnline, Pancreas., vol. 26, No. 1, pp. 1-7, (Jan. 26, 2003).

Henniges, "Enzyme Replacement Therapy—A Therapeutic Regimen for Pancreaic Exocrine Insufficiency", Business Briefing: European Pharmacotherepy, (2005).

"Food Chemicals Codex", Committee on Food Chemicals Codex Food and Nutrition Board, Institute of Medicine of the National Academies, pp. 894-927, Copyright 2003.

IUBMB Enzyme Nomenclature, EC 3.4.21.63, retrieved from the Internet at: http://www.chem.qmw.ac.uk/iubmb/enzyme/EC3/4/21/63.html on Dec. 23, 2004.

"Protease P 'Amano' 6", pp. 1-3, (Aug. 20, 2003).

Deerland Fungal Amylase Concentrate: Fungal Amylase, retrieved from the Internet at: http://www.deerland-enzymes.com/index.cfm?fuseaction=browse&id=14001&pageid=52 on Dec. 23, 2004.

Alpha-Amylase from *Aspergillus oryaze*, Var., published in FNP 52 Add 8, (2000), retrieved from the Internet at: http://apps3.fao.org/jecfa/additive_specs/docs/8/additive-0793.htm on Dec. 23, 2004.

2.2.3 Alpha-Amylases, York Structural Biology Laboratory, retrieved from the Internet at http://www.ysbl.york.ac.uk/projects/2/2.2.3.htm on Dec. 23, 2004.

Deerland Bromelain: A Plant Protease for Protein Hydrolysis, pp. 1-2, retrieved from the Internet at: http://www.deerland-enzymes.com/index.cfm?fuseaction=browse&id=14001&pageid=55 on Dec. 23, 2004.

Papain Concentrate: Concentrated Protease Enzyme, retrieved from the Internet at: http://www.deerland-enzymes.com/index.cfm?fuseaction=browse&id=14001&pageid=45 on Dec. 23, 2004.

Bio-Cat, Inc. Products and Services, Enzyme Products, pp. 1-4, retrieved from the Internet at: http://www.bio-cat.com/products.html on Apr. 5, 2004.

Johns Hopkins Division of Pulmonary & Critical Care Medicine: Pulmonary Health Clinical Conditions, Cystic Fibrosis—Treatment, pp. 1-7, retrieved from the Internet at: http://www.hopkins-lungs.org/programs/cf/treatment.shtml on Mar. 23, 2004.

South African Electronic Package Inserts: Viokase® Tablets, pp. 1-2, retrieved from the Internet at: http://home.intakeom.com/pharm/lennon/viokase.html on Mar. 25, 2004.

ChrioWeb.com: Proteolytic Enzymes—part 3, pp. 1-4, retrieved from the Internet at: http://www.chrioweb.com/archives/print_friendly.php?volume=09&issue=25&issue_date=... on Aug. 29, 2005.

Welcome to Truestar Health Encyclopedia—Digestive Enzymes, pp. 1-5, retrieved from the Internet at: http://www.truestarhealth.com/Notes/2840008.html on Dec. 23, 2004.

Enzyme Technical Association—Industry Guidelines for the Use of Enzyme Dietary Supplements, pp. 1-11, retrieved from the Internet at: http://www.enzymetechnicalassoc.org/dietary.html on Dec. 28, 2004.

International Search Report of PCT/US2006/042466, 2008.

Written Opinion of PCT/ US2006/042466, 2008.

Xu et al., "Immobilization of *Candida cylindracea* lipase on methyl acrylate-divinyl benzene copolymer and its derivatives," Enzyme and Microbial Technology, vol. 17, 1995, pp. 194-199.

\* cited by examiner

Activity Profiles for *Candida rugosa*

Effect of pH on Stability for *Candida rugosa*

Activity Profiles for *Rhizopus niveus* Amyloglucosidase

Activity Profiles for Papain

Activity Profiles for Bromelain

Activity Profiles for *Rhizopus niveus* Protease

Activity Profiles for *Aspergillus niger* Protease

Activity Profiles for *Aspergillus oryzae* Lactase

Yeast Lipase: Fatty Acid Specificity

COMPOSITION WITH A FUNGAL (YEAST) LIPASE AND METHOD FOR TREATING LIPID MALABSORPTION IN CYSTIC FIBROSIS AS WELL AS PEOPLE SUFFERING FROM PANCREATIC LIPASE INSUFFICIENCY

CROSS-REFERENCE TO RELATED APPLICATIONS

This application is the U.S. National Stage filing of International Application No. PCT/US2006/042466, filed Oct. 31, 2006, which claims the benefit of U.S. Provisional Patent Application No. 60/731,813, filed Nov. 1, 2005, the disclosures of each of which are hereby incorporated by reference.

BACKGROUND OF THE INVENTION

1. Field of the Invention

The invention relates to a composition and method for treating pancreatic enzyme insufficiency, particularly lipid malabsorbtion associated with cystic fibrosis.

2. Description of Related Art

Various diseased states such as pancreatitis, pancreatectomy and cystic fibrosis yield a condition in which insufficient digestive enzymes, particularly pancreatic enzymes, are available for the digestive process. Since the early part of the $20^{th}$ century, pancreatic enzyme supplements derived from animal sources have been available for oral administration to patients with pancreatic enzyme deficiencies.

Pancreatic enzymes are active under near neutral and slightly alkaline conditions and under normal digestive processes would enter the digestive process in the duodenum where the pH conditions are favorable. However, when exogenous pancreatic enzymes are administered by an oral route, a problem exists, because animal derived pancreatic enzymes are not stable in the acid conditions of the stomach (pH 2.5 to 4), and a considerable portion of the exogenously administered pancreatic enzyme (if not all) is irreversibly inactivated.

Two approaches have been proposed for addressing this problem. Sipos has proposed encoating a pancreatic enzyme preparation in gastric acid resistant microspheres. (See U.S. Pat. Nos. 5,260,074; 5,324,514; 5,352,460; 5,405,621, for example, for detailed discussions of pancreatic enzyme preparations encapsulated in acid resistant microspheres and methods of making such preparations.)

Such compositions may be resistant to gastric juices but may be less than satisfactory for at least two reasons. First, studies by Graham (New England Journal of Medicine 296: pp. 1134-1317, Jun. 9, 1977) show that enteric-coated tablets were substantially less effective in steatorrhea reduction than uncoated tablets or capsules. Secondly, although the enteric coating has the theoretical advantage of allowing the enzyme preparation to pass through the hostile environment of the stomach to the small intestine where alkaline conditions should be more favorable to the pancreatic enzymes, the latter condition may not be met in patients with pancreatic insufficiency because the upper regions of the small intestine, e.g. the duodenum and upper jejunum are often acidic. Accordingly, the enzymes may not be released as anticipated and/or may still be inactivated by acidic conditions.

A second approach, suggested in U.S. Patent Applications 2001/0046493 and 2003/0017144, is the use of cross-linked lipase crystals in preparations for the treatment of pancreatic insufficiency. Cross-linking is believed to enhance the lipase's resistance to low pH. However, preparing cross-linked lipase involves significant preparation steps to prepare the cross-linked material, increasing the cost and difficulty of preparing the therapeutic agent.

Traditionally enzymes from animal sources have been used as exogenous sources for preparation of enzyme compositions for treatment of pancreatic insufficiency; animal derived pancreatic enzymes need bile acids or salts for proper activation. In diseases like cystic fibrosis, the secretion and/or availability of bile acids or salts is impeded by the mucus build up associated with the diseased state. Some pancreatic enzyme preparations include bile salts in addition to animal derived pancreatic enzymes. See, for example, U.S. Pat. No. 5,750,104.

In yet another approach, Galle, et al., in U.S. Patent Application 2004/0057944 discloses a microbial enzyme mixture as an alternative to animal enzymes for treating pancreatic insufficiency, including the insufficiency associated with cystic fibrosis. The composition of Galle, et al., includes a lipase from *Rhizopus delemor*, a protease from *Aspergillus melleus* and an amylase from *Aspergillus oryzae*, which have good pH stability and activity in the pH range of pH 4-8. The pH range in the stomach is typically pH 2.5-4. Hence, transit through the stomach exposes these enzymes to unfavorable conditions.

Accordingly, there remains a need for improved pancreatic enzyme preparations for treating pancreatic enzyme insufficiencies which can maintain their activity under the acid conditions of the stomach and perform their function in the small intestine with a high level of efficacy.

SUMMARY OF THE INVENTION

It is an object of this invention to provide an improved composition for treatment of pancreatic insufficiency.

It is another object of this invention to supplement current therapy for cystic fibrosis by supplying improved digestive aids for use by cystic fibrosis patients.

These and other objects of this invention are provided by one or more of the following embodiments.

In one embodiment, this invention provides a digestive enzyme composition comprising at least one lipase, and optionally at least one amylase or amyloglucosidase, and at least one protease, each of these enzymes being stable under acid conditions and active under acid-to-neutral conditions. Preferably, the lipase and the amylase or amyloglucosidase are derived from microbial sources, more preferably from *C. cylindracea* (lipase) and *R. niveus* (amyloglucosidase). Also preferably, the protease is derived from a plant source, more preferably papain or bromelain, and/or *R. niveus*. In another embodiment, the composition also comprises a microbial lactase.

In a preferred embodiment, the digestive enzyme composition according to this invention comprises a lipase from *C. cylindracea*, a protease from *R. niveus, A. niger*, bromelain and/or papain, amylase and/or amyloglucosidase, and lactase, all enzymes except the bromelain and papain being from microbial sources.

In another embodiment, this invention provides a new method of treating patients with pancreatic insufficiency by administering a digestive enzyme composition according to this invention substantially contemporaneously with food. In an alternative embodiment, one or more of the enzymes are administered separately, so long as all of the enzymes are ingested substantially contemporaneously with each other and with the food to be digested. The method of this invention is particularly developed for use in treating patients having cystic fibrosis.

BRIEF DESCRIPTION OF THE DRAWINGS

The invention will be described in further detail hereinafter with reference to the accompanying figures in which.

DETAILED DESCRIPTION OF PREFERRED EMBODIMENTS

Figure 1:
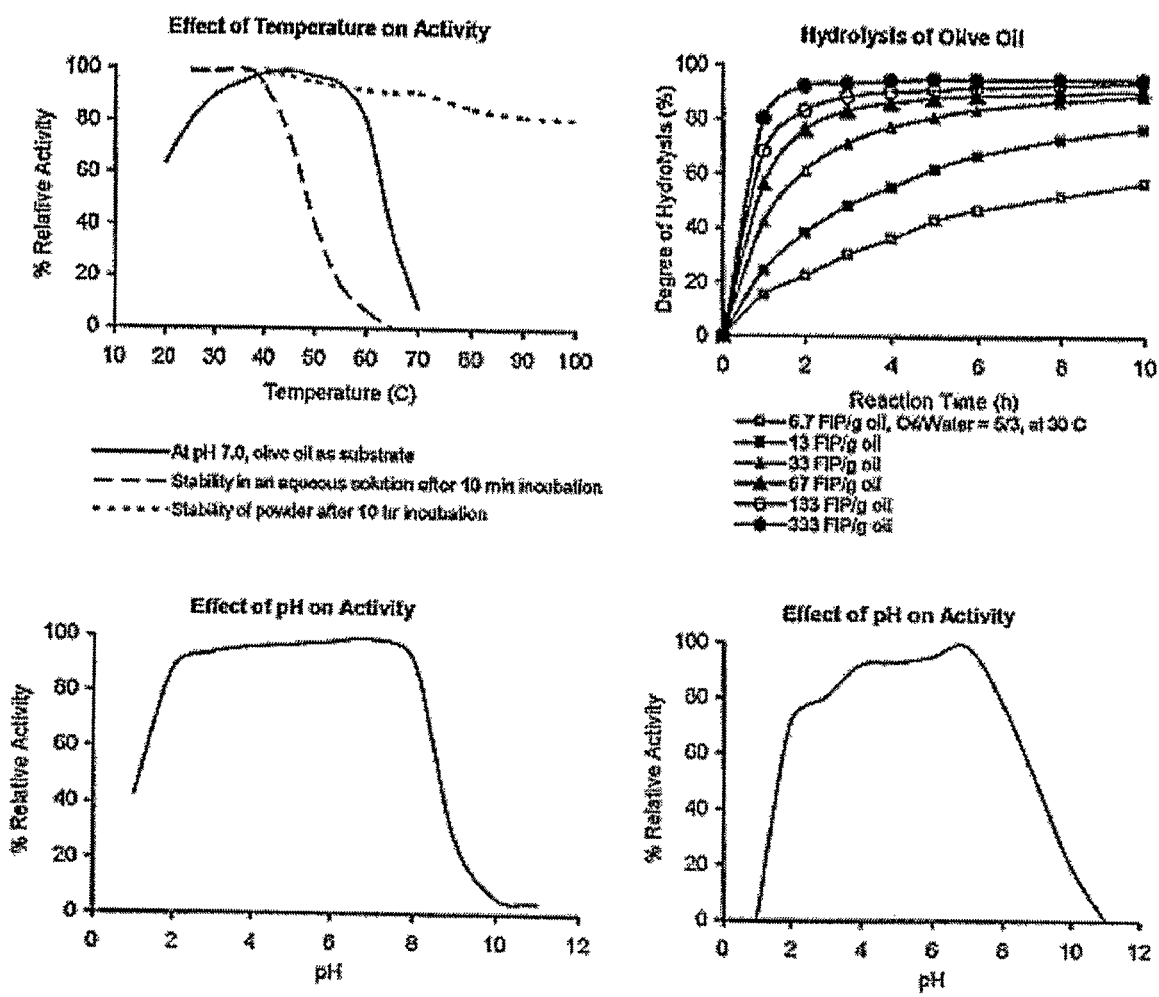
FIG. 1 is a graph showing the effect of pH on activity for lipase preparation of *Candida rugosa* (also referred to as *C. cylindracea*).

The invention provides improved enzyme compositions for treatment of pancreatic insufficiency. In some embodiments, the improved composition comprises a lipase, an amylase or amyloglucosidase and at least one protease obtained from microbial and/or plant sources. In some embodiments the composition further comprises a lactase. The enzymes selected for this composition are stable under acid and/or acid-to-neutral conditions (i.e., they retain a high level of activity upon prolonged exposure to acid and/or acid-to-neutral conditions). Methods of preparing compositions of the invention are also provided herein. Compositions of the invention may be used to treat patients suffering from pancreatic enzyme insufficiency and/or steatorrhea.

Several types of pancreatic disorders can lead to pancreatic enzyme insufficiency. These include pancreatic cancer, chronic pancreatitis and pancreatectomy. Pancreatic insufficiency also appears as a genetic disease, particularly in dogs.

One particularly serious type of such disorder is cystic fibrosis which is a genetic disease. With the possible exception of experimental gene therapy treatments, no cure or method of prevention of the disease is known. Patients suffering from cystic fibrosis have problems digesting their food due to their inability to secure pancreatic and biliary secretions in the small intestine. Pancreatic secretions in patients with cystic fibrosis have reduced water content, and the intestinal walls clog with thick mucus. As the disease progresses many problems may manifest, including such problems as the pancreas autodigesting, further impairing availability of pancreatic enzymes, and the patient's stools becoming large and bulky due to a high amount of undigested fat.

Additionally, cystic fibrosis patients have reduced bicarbonate secretion which impairs the normal process of neutralization of acidic materials passing from the stomach into the small intestine. This also impairs the efficiency of performance of human (or exogenously supplied animal) pancreatic enzymes as they perform optionally at neutral to alkaline pH and may even be irreversibly inactivated upon exposure to low (acidic) pH. The mucus secretions associated with cystic fibrosis also impair secretion of bile acids and salts. Sodium taurocholate is needed to activate animal derived pancreatic lipase. Thus, the reduced availability of necessary bile salts further impairs the function of animal-derived lipase.

As the digestive process of the small intestine is interrupted in diseases like cystic fibrosis due to the unavailability and/or reduced activity of multiple digestive enzymes in the upper small intestine, replacement or supplementation of lipase, amylase and proteases are needed to ensure adequate digestion of food consumed. As discussed above, providing replacement by oral supplementation with enzymes from animal sources is problematic, as ingested enzyme supplements must transit the stomach, and such enzymes from animal sources are adversely effected by exposure to the acidic conditions of the stomach. Further, the diseased state may create conditions in the upper small intestine that are on the acid side of neutral, rather than the normal condition of neutral to slightly alkaline. Animal derived pancreatic enzymes typically have optimal activity and stability at neutral to alkaline pH, so they are inactivated during transit of the stomach and their activity is also reduced by relatively low pH conditions of the upper intestine.

The present invention addresses this problem by providing a composition comprising a lipase, optionally combined with an amylase or amyloglucosidase, at least one protease derived from a plant, microbial or fungal source and/or lactase, each specifically selected as an enzyme that retains its activity when exposed to acidic conditions of about pH 2.0 to about pH 7.0, preferably about pH 3.0 to about pH 7.0, about pH 3.0 to about pH 5.0, more preferably pH 3.5 to 4.5 (e.g., acidic conditions of the stomach) during transit of food through the stomach (e.g., for approximately 3 hours). Preferably, the enzymes will also exhibit a substantial level of activity (relative to their maximal activity) at acid-to-neutral pH values (i.e., pH=4-8), so that digestion will occur in the upper end of the small intestine, as pH rises relatively slowly, due to the disease state. More preferably, the enzyme composition contains at least one protease which is active under the acid conditions of the stomach, and another protease which is stable in the stomach, but active at more neutral pH (i.e., pH=4-8). With the complementary proteases of this more preferred embodiment, protein digestion begins in the stomach (as does pepsin digestion in disease-free individuals) and continues even as pH rises through the intestine.

An enzyme is "stable" when it retains at least 50% of its initial activity for at least 30 minutes. Preferably, a stable enzyme will retain at least 60%, more preferably 70%, 75%, 80%, 85%, 90%, 95%, or most preferably about 100% of its initial activity for at least 30 minutes, more preferably about one hour, more than one hour, about three hours, more than three hours, about 5 hours or most preferably more than five hours. An enzyme is considered stable under acid conditions if the residual activity of the enzyme after incubation at pH=3 is at least 50% of the activity retained upon incubation under identical conditions except that the pH of incubation is the pH at which the enzyme exhibits optimum activity. More preferably, acid stable enzymes retain at least 70% as much activity upon incubation at pH=3 as at their activity optimum pH, even more preferable, they retain at least 80% or 85%. An enzyme is active under acid-to-neutral conditions if it exhibits maximum activity between pH=4.0-8.0 and also exhibits at least 70% of its maximal activity over a range of at least 1.5 pH units between pH=4.0-8.0. For example, an enzyme that is stable under acidic conditions retains at least 50% of its initial activity at a pH range of about pH 2.0 to about pH 4.0 for at least 30 minutes. In another example, an enzyme that is stable under acid-to-neutral conditions retains at least 50% of its initial activity at a pH range from about pH 5.0 to about pH 6.5 for at least 30 minutes.

In a preferred embodiment of the composition of the invention, a lipase from *Candida cylindracea* (also known as *C. rugosa*), optionally combined with an amylase or amyloglucosidase from *Rhizopus niveus*, at least one protease such as a papain protease, bromelain protease, *A. niger* acid protease, *R. niveus* protease and/or a combination thereof and/or lactase, is provided as an oral enzyme supplement for treating patients suffering from pancreatic enzyme insufficiency. As FIGS. 1-7 show, these enzymes have good stability in the pH ranges of 2.0 to 5.0. Further, as the figures show, these enzymes retain a high percentage of their maximal activity under acidic and/or acid-to-neutral conditions.

Figure 2:
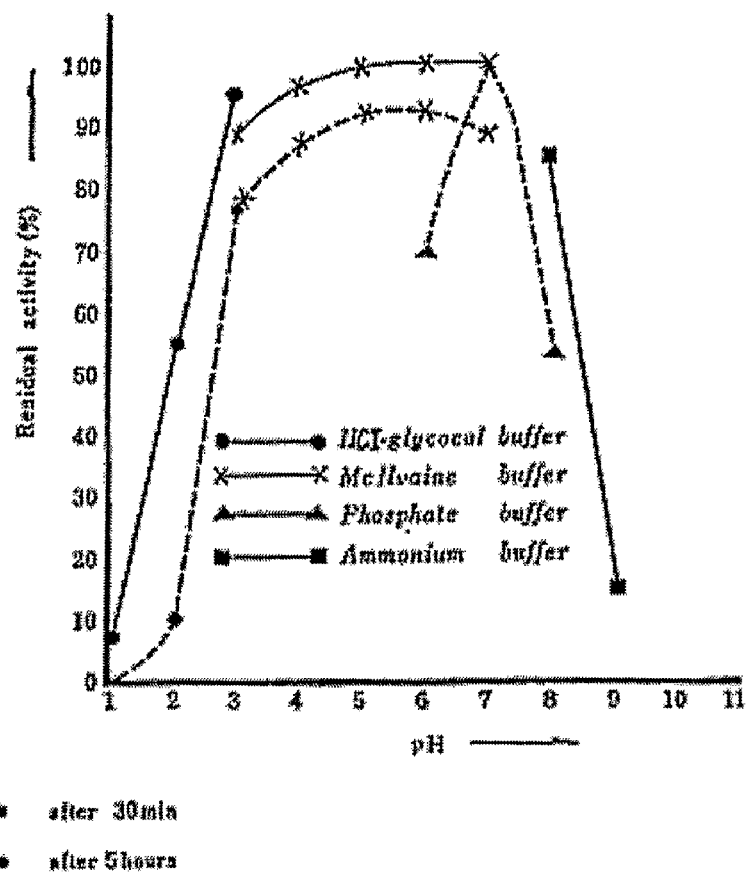
FIG. 2 is a graph showing the effect of pH on stability for lipase preparation of *C. rugosa* (also referred to as *C. cylindracea*).
Figure 3:
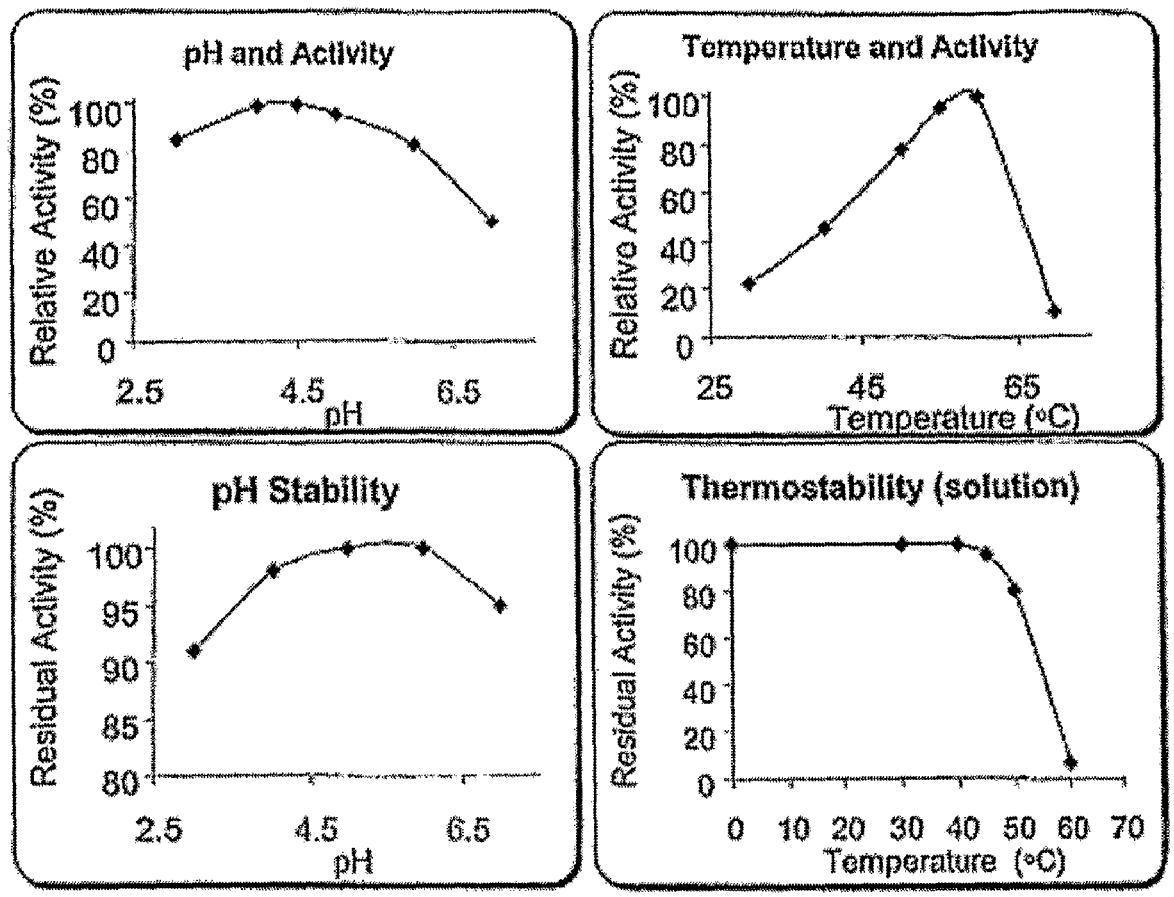
FIG. 3 is a graph of the pH vs. activity profile and a graph of pH vs. stability for *Rhizopus niveus* amyloglucosidase.

Exemplary lipases suitable for use in the invention include fungal lipases, preferably yeast lipases. In a preferred embodiment, the fungal lipase of the invention is *C. cylindracea* lipase. FIGS. 1 and 2 show that lipase from *C. cylindracea* shows good activity (e.g., over 80% of its maximal activity) between pH=3-7 (FIG. 1) over a sustained period of time (e.g., from over 30 minutes to over 5 hours, FIG. 2). FIGS. 1 and 2 show that neither activity nor stability of lipase from *C. cylindracea* will be affected by changes in pH that occur throughout the digestive system. Thus, the lipase will be effective as it travels throughout the digestive process (e.g., from the stomach to the small intestine), thereby delivering the necessary enzyme to a patient in need thereof (e.g., to a patient afflicted with lipase pancreatic insufficiency).

Figure 9:
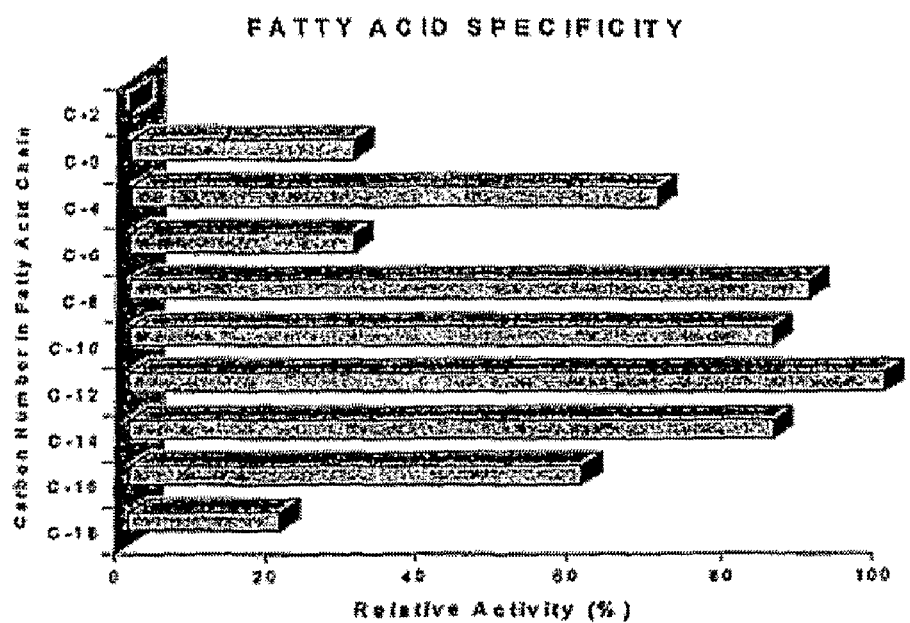
FIG. 9 shows that lipase derived from *C. rugosa* (also referred to as *C. cylindracea*) has broad specificity towards short, medium and long fatty acid chains. To prepare the substrate solution (for the pNP Method) 2.64 mM pNP-compounds is dissolved in 190 ml of 52.6 mM acetone buffer (pH 5.6) containing 2.1% Triton X-100 at 60° C. 0.05 ml of enzyme solution is added to 0.95 ml of substrate solution pre-incubated at 37° C. for 5 min. After the incubation for 15 min. at 37° C., the reaction is stopped by the addition of 2 ml of acetone and the increase in absorbance at 410 nm of the reaction mixture is measured relative to a control reaction mixture. For the control reaction, enzyme solution is added after the addition of acetone.

Use of fungal, microbial and/or plant lipases offer the further advantages of not requiring bile salts for activation. Thus, the lack of bile salts due to a diseased state such as cystic fibrosis does not impact the activity of the fungal lipase (e.g., lipase of *C. cylindracea*), and accordingly, the need to include bile acids or salts in exogenous enzyme compositions for treating pancreatic enzyme insufficiency is eliminated. In particular, *Candida* lipase is advantageous because it does not need a bilary activator, and furthermore, it is non-specific in contrast to pancreatic lipase which will only hydrolyze the 1-3 bonds of a triglyceride (i.e., *C. cylindracea* lipase will hydrolyze all three fatty acid bonds of a triglyceride). In addition, *Candida* lipase has broad specificity towards short, medium and long chain fatty acids (see e.g., FIG. 9). Furthermore, *C. cylindracea* demonstrates greater than 80% of its maximal activity at various pHs, including pH 4 (see e.g., FIG. 1).

Figure 4:
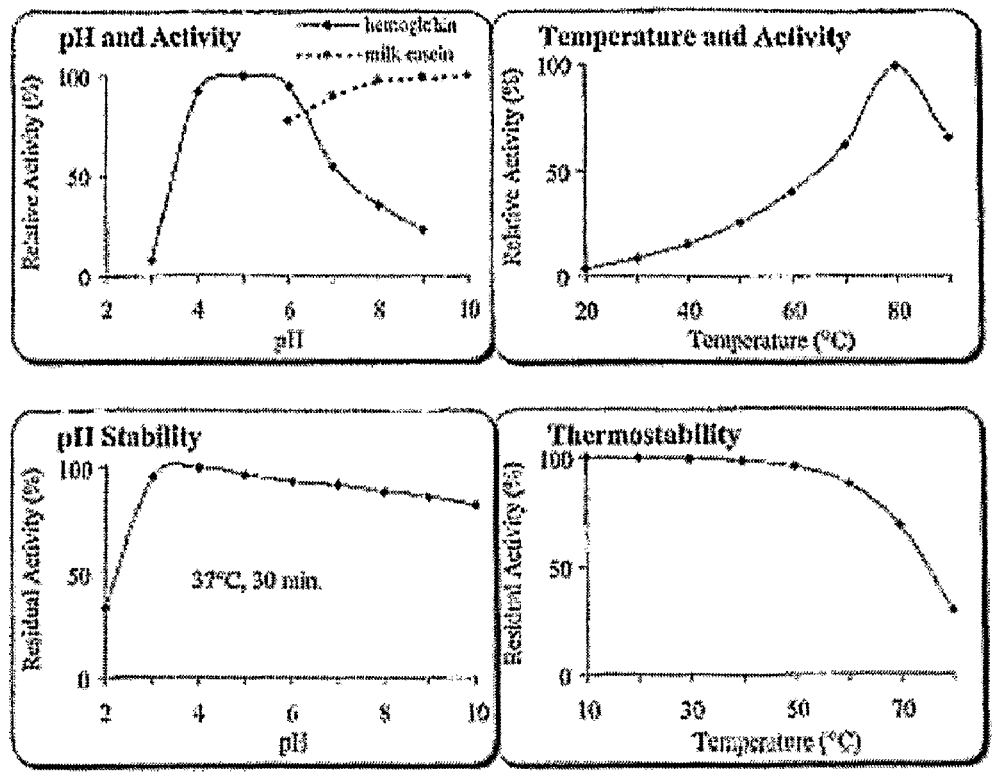
FIG. 4 is a graph of the pH vs. activity profile and a graph of pH vs. stability for protease preparation from papain.

Exemplary proteases suitable for use in the invention include protease obtained from *Aspergillus niger* (see e.g., FIG. 7), *R. niveus* fermentation (see, e.g., FIG. 6), bromelain from pineapple stem (see, e.g., FIG. 5) and papain obtained from papaya latex extraction (see, e.g., FIG. 4).

A single protease may be used in the composition of the invention, but using multiple proteases from different sources can provide additional advantages. In particular, different proteases from different sources having different specificity may be used. As the chemical bond makeup of different foods vary, providing multiple proteases with different specificities facilitates more complete breakdown of proteins and peptides into amino acids in the digestive process. In a preferred embodiment, one or more of a protease from papain, bromelain, *R. niveus*, *A. niger*, and/or a fungal protease can be used. In another embodiment, an acid protease is used in conjunction with a protease that is active within the acid-to-neutral range. For example, in a preferred embodiment, an acid protease from *A. niger* is used with papain or bromelain. In another example, proteases from *A. niger* and *R. niveus* are used in conjunction with papain and/or bromelain. Typical activity levels of suitable proteases include about 1,800 SAPU units/g of acid protease activity for *R. niveus* protease, about 2,500 SAPU units/g of acid protease activity for *A. niger* protease, about 75,000 PU/mg for papain protease activity, and 50,000 PU/mg for bromelain protease activity. In exemplary embodiments, 25 mg of papain (activity of 75,000 PU/mg), 25 mg of bromelain (activity of 50,000 PU/mg), 50 mg of acid protease (activity of 1,800 SAPU units/g) can be used alone or in combination.

Figure 5:
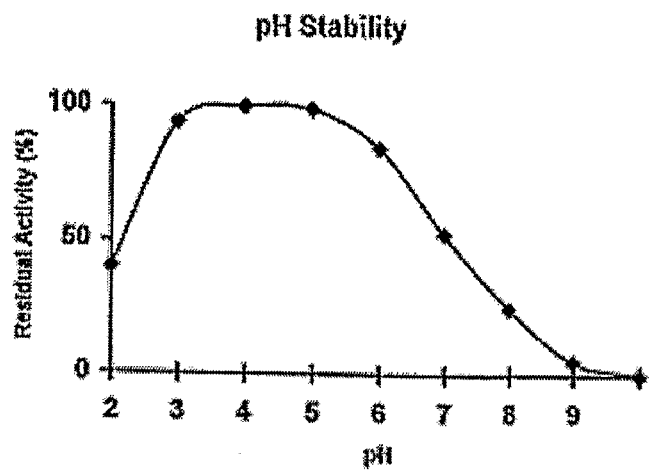
FIG. 5 is a graph of the pH vs. activity profile for protease preparation from bromelain.
Figure 5:
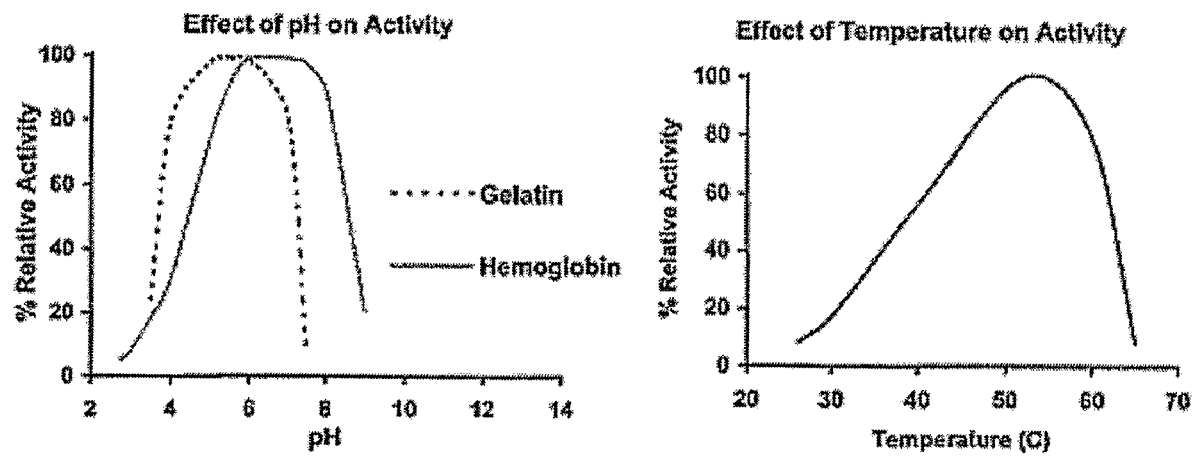
Figure 6:
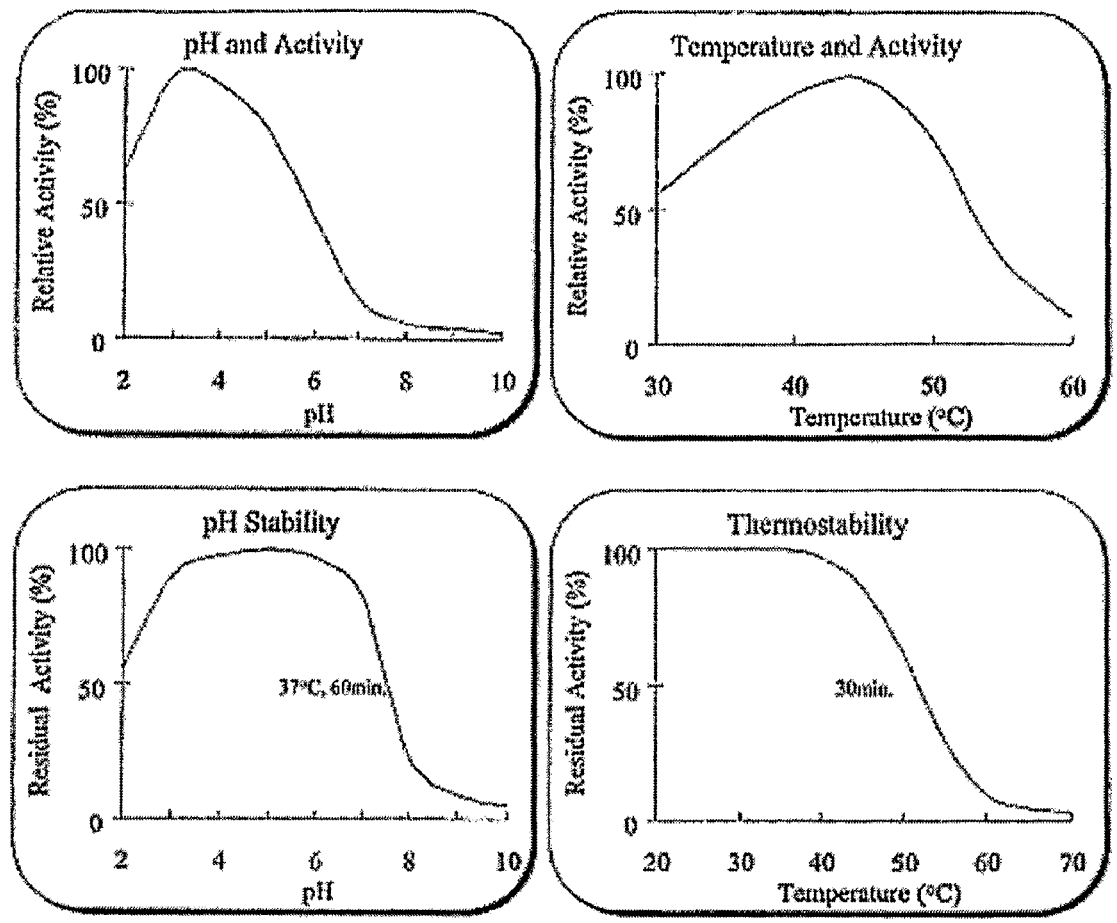
FIG. 6 is a graph of the pH vs. activity profile and a graph of pH vs. stability for acid protease preparation from *R. niveus*.
Figure 7:
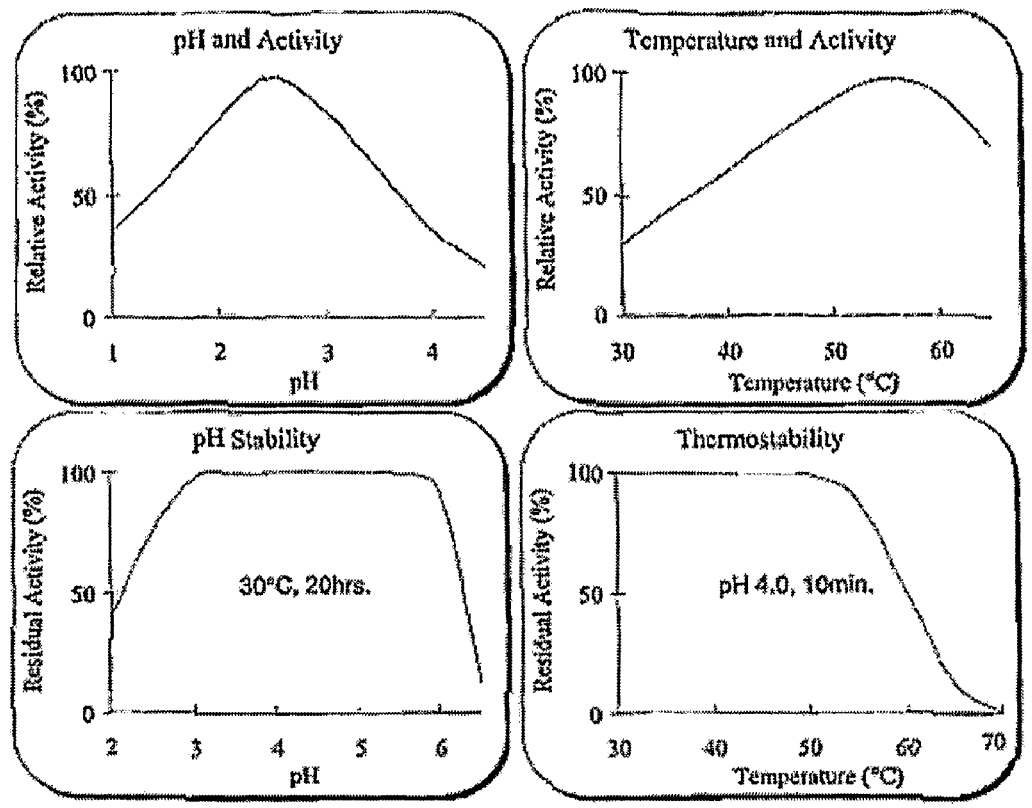
FIG. 7 is a graph of the pH vs. activity profile and a graph of pH vs. stability for protease preparation from *Aspergillus niger*.

FIGS. 4 and 5 show that papain and bromelain, respectively, both exhibit good activity between pH=4-8, although their activity falls off rapidly below pH=4. However, their stability curves show that they retain activity well across a range from pH=3-7, so after passing through the acid conditions of the stomach, they will survive to be active as the pH rises in the intestine.

The composition of this invention may also comprise an amylase and/or an amyloglucosidase. In one embodiment, the amylase or amyloglucosidase is a fungal amylase. In a preferred embodiment, the amylase or amyloglucosidase is from *R. niveus* or *A. oryzae*. *R. niveus* shows good activity and stability from pH 3-6 (see, e.g., FIG. 3), indicating that it will promote digestion in the stomach as well as the intestine. Amyloglucosidase has the capability of reducing starch and/or dextrin's to glucose which is readily absorbed in the small intestines. Typical activity levels of suitable amylases or amyloglucosidases include about 1,000 AG/gm units of activity for *R. niveus* amylase and about 100,000 SKB/gm units of fungal amylase activity for *A. oryzae*.

The composition may, in some embodiments, further comprise a lactase. Milk contains the sugar lactose which is typically present in an amount of about 5% in milk. If this sugar is not hydrolyzed in the small intestine it can cause digestive problems. Lactase, which hydrolyzes lactose, is produced in the brush border region of the small intestine. The intestinal mucus deposits associated with cystic fibrosis may impair availability of lactase and/or the altered pH conditions of the small intestine may result in an insufficiency of lactase and/or reduced activity. This may yield the condition known as lactose intolerance. For those afflicted for lactose intolerance, lactose is not hydrolyzed in the small intestine and thus passes to the large intestine where bacteria produce acid and gas causing bloating and in some cases diarrhea.

Figure 8:
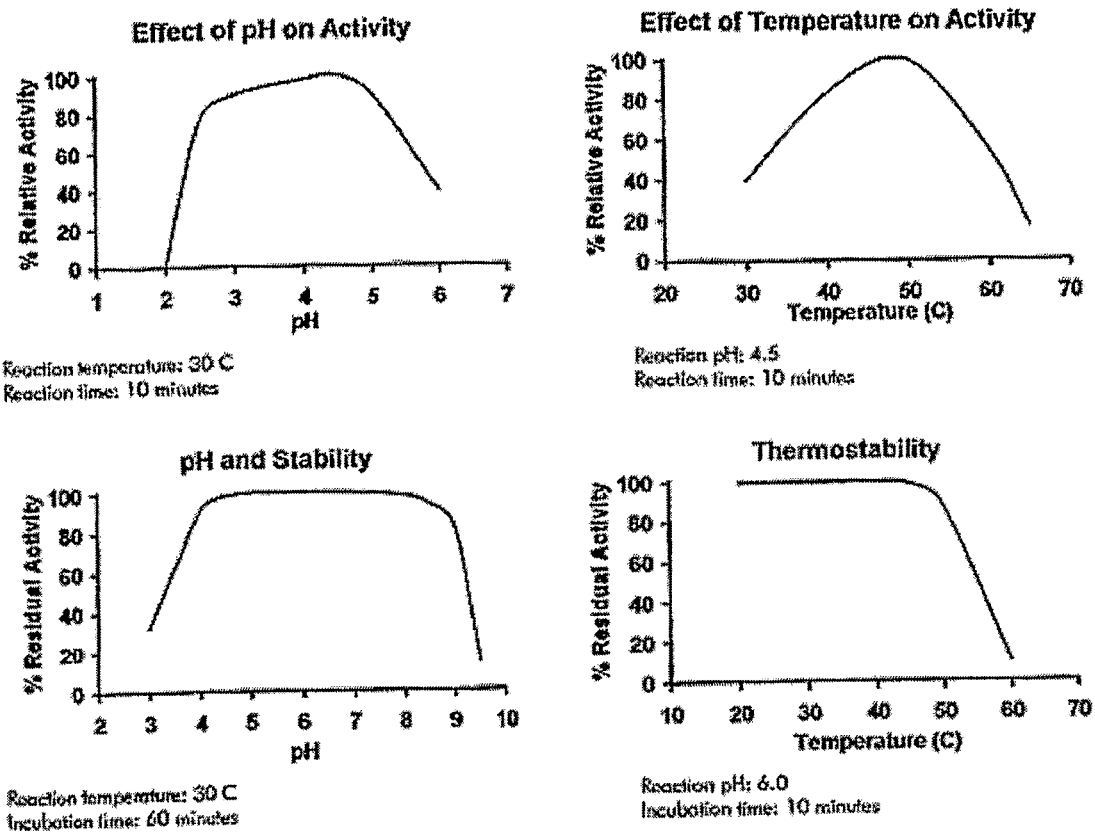
FIG. 8 is a graph of the pH vs. activity profile and a graph of pH vs. stability for lactase preparation from *A. oryzae*.

Inclusion of lactase in the enzyme composition of the invention may alleviate the lactose intolerance condition frequently associated with cystic fibrosis. For example, lactase from *A. oryzae* is active and stable at a low pH (e.g., see FIG. 8). Lactase from *A. oryzae* may be supplied as capsules containing 9000 ALU/g, and two capsules are typically recommended per meal.

As indicated above, the invention contemplates using various combinations of enzymes. Tables 1 and 2 below describe activity and stability profiles for exemplary enzymes contemplated for use in the present invention. Any combination of the enzymes listed in Tables 1 and 2 are contemplated for use in the present invention.

TABLE 1

Enzyme pH Ranges for Activity and Stability

| Enzyme | Activity % of maximal activity | Stability % of initial activity (temperature and length of storage) |
|---|---|---|
| Acid Protease From *Aspergillus niger* | 40% @ pH 1<br>70% @ pH 2<br>90% @ pH 2.5 | 45% @ pH 2<br>95% @ pH 3<br>95% @ pH 6<br>10% @ pH 7<br>(20 hours at 30° C.) |
| Acid Protease From *Rhizopus niveus* | 65% @ pH 2<br>90% @ pH 4<br>20% @ pH 6 | 60% @ pH 2<br>100% @ pH 4<br>100% @ pH 7<br>(60 minutes at 37° C.) |
| Papain | 10% @ pH 3<br>95% @ pH 4<br>95% @ pH 6<br>40% @ pH 7 | 40% @ pH 2<br>100% @ pH 3<br>90% @ pH 5<br>80% @ pH 7<br>(30 minutes at 37° C.) |
| Bromelain | 10% @ pH 3<br>20% @ pH 4<br>100% @ pH 6<br>100% @ pH 7 | 10% @ pH 2<br>50% @ pH 3<br>100% @ pH 7<br>(30 minutes at 37° C.) |
| *Candida cylindracea* Lipase | 50% @ pH 2<br>60% @ pH 3<br>70% @ pH 4 | 50% @ pH 2<br>95% @ pH 3<br>100% @ pH 6<br>100% @ pH 7<br>(30 minutes)<br>10% @ pH 2<br>80% @ pH 3<br>90% @ pH 6<br>85% @ pH 7<br>(after 5 hours) |
| *Rhizopus niveus* Amyloglucosidase | 30% @ pH 2<br>80% @ pH 2.5<br>100% @ pH 5<br>30% @ pH 7 | 90% @ pH 2.5<br>95% @ pH 4<br>90% @ pH 5<br>90% @ pH 7<br>(60 minutes at 39° C.) |
| *A. oryzae* Lactase | 50% @ pH 3<br>70% @ pH 4<br>95% @ pH 5<br>50% @ pH 6<br>10% @ pH 7 | 20% @ pH 3<br>80% @ pH 4<br>100% @ pH 6<br>100% @ pH 7<br>(60 minutes) |

TABLE 2

Activity Profiles

| Enzyme | At Least 50% of Its Maximal Activity | At Least 70% of Its Maximal Activity | At Least 80% of Its Maximal Activity |
|---|---|---|---|
| Acid Protease From *A. niger* | pH 1.5 to 3.5 | pH 2 to at least 3 | pH 2 to at least 3 |
| Acid Protease From *R. niveus* | pH 2.0 to about 5.5 | pH 2.5 to at least 5 | pH 2.5 to at least 5 |
| Papain | about pH 3.5 to 7 | pH 4 to 6.5 | pH 4 to 6.5 |
| Bromelain | about pH 4 to at least 7.5 (Gelatin);<br>about pH 5 to at least 8.5 (Hemoglobin) | about pH 4 to about 7.5 (Gelatin);<br>about pH 5 to at least 8.5 (Hemoglobin) | about pH 4 to about 7.5 (Gelatin);<br>about pH 5 to at least 8 (Hemoglobin) |
| *C. cylindracea* Lipase | pH 2 to at least 8 | about pH 4 to 8 | about pH 5 to 8 |
| *R. niveus* Amyloglucosidase | at least pH 2.5 to 6 | at least pH 2.5 to 6 | at least pH 2.5 to 6 |
| *A. oryzae* Lactase | pH 2.5 to 6 | pH 2.5 to 5.5 | pH 2.5 to 5 |

The invention also contemplates using enzymes or any combination of enzymes that are "substantially similar" to the enzymes listed in Table 2. An enzyme is "substantially similar" to an enzyme listed in Table 2 if the enzyme has an activity profile within the range listed for a particular enzyme. For example, an enzyme that is "substantially similar" to an Acid Protease from *R. niveus* has the following activity profile:

| Enzyme | At Least 50% of Its Maximal Activity | At Least 70% of Its Maximal Activity | At Least 80% of Its Maximal Activity |
|---|---|---|---|
| Enzyme "substantially similar" to an Acid Protease From *R. niveus* | pH 2.0 to about 5.5 | pH 2.5 to at least 5 | pH 2.5 to at least 5 |

For pharmaceutical preparations prepared according to the invention, orally administered dosage forms are convenient. Such dosage forms may include, for example, powders, pellets or microspheres, which may optionally be filled into capsules or sachets or be compressed to form tablets. Liquid pharmaceutical preparations such as suspensions or solutions are also contemplated. The individual enzymes (e.g. the lipase, the protease or proteases, the amylase and in some embodiments a lactase) may be presented together in a mixture or spatially separated from each other. If the individual enzymes are not spatially separated from each other, dry processing and/or dry storage is preferable.

The pharmaceutical preparations may further contain conventional excipients and/or carriers. Such excipients and carriers are well known to those skilled in the art. Such excipients and/or carriers include, for example, microcrystalline celluloses, maltodextrin, polyethylene glycols, alcohols, surfactants and flavorants.

The microbial and plant enzymes used in the practice of the invention have good stability over a wide pH range, particularly at acid and neutral pH conditions, and can therefore be used without further treatment (such as film-coating) directly for the preparation of orally administered pharmaceutical preparations. For storage, handling and administration, the individual enzymes may be granulated together or spatially separated from each other. The granulated material may optionally be film-coated. Accordingly, if the enzymes are pelletized individually, one enzyme may be coated while the others are not. As described above, enteric coating is not needed for the composition of the invention, however coating to improve palatability or protect from moisture or air, for example, may be optionally desirable in some embodiments.

Typically, the enzyme preparation of the invention is administered to a patient with a pancreatic enzyme deficiency with each meal at the time that the meal is consumed. Compositions of the invention are preferably administered to a patient "substantially contemporaneously" with food. A composition is administered to a patient "substantially contemporaneously" with food if the composition is ingested at a time during or after ingestion of the food. When a composition is administered to a patient substantially contemporaneously with food, the composition is ingested at a time during or after ingestion of the food so that at least 50% of the composition passes from the stomach to the intestine during the period when the majority of the food passes from the stomach to the intestine. Alternatively, a composition is administered substantially contemporaneously if it is ingested within an hour of ingestion of the food. In a particularly preferred embodiment, the composition is administered after ingestion of food. In some embodiments, a single capsule or tablet is administered during or after ingestion of food. In other embodiments, two or more capsules or tablets are administered during or after ingestion of food. In a preferred embodiment, the capsule or tablet contains no more than 250 mg of active ingredients.

EXAMPLES

Example A

A 250 mg Capsule or Tablet Containing 1) 75 mg of *C. cylindracea* lipase;
2) 20 mg of papain, 20 mg of bromelain, and 25 mg of acid protease from *A. niger* or *R. niveus* protease;
3) 40 mg of amylase or amyloglucosidase;
4) 25 mg lactase; and
5) 45 mg of excipient.

Example B

A 250 mg Capsule or Tablet Containing 1) 75 mg of *C. cylindracea* lipase;
2) 20 mg of papain, 20 mg of bromelain, and 25 mg of acid protease from *A. niger* or *R. niveus* protease;
3) 40 mg of amylase or amyloglucosidase; and
4) 70 mg of excipient.

Example C

A 250 mg Capsule or Tablet Containing 1) 75 mg of *Candida cylindracea* lipase;
2) 25 mg of papain, 25 mg of bromelain, and 25 mg of acid protease from *A. niger* or *R. niveus* protease;
3) 50 mg of amylase or amyloglucosidase; and
4) 50 mg of excipient.

Example D

A 250 mg Capsule or Tablet Containing 1) 75 mg of *C. cylindracea* lipase;
2) 40 mg of *R. niveus* protease;
3) 40 mg of amylase or amyloglucosidase;
4) 50 mg lactase; and
5) 45 mg of excipient.

Example E

A 250 mg Capsule or Tablet Containing 1) 75 mg of *C. cylindracea* lipase;
2) 20 mg of *R. niveus* protease and 20 mg of *A. niger* protease;
3) 40 mg of amylase or amyloglucosidase;
4) 50 mg lactase; and
5) 45 mg of excipient.

Example F

A 250 mg Capsule or Tablet Containing 1) 75 mg of *C. cylindracea* lipase;
2) 20 mg of papain and 20 mg of bromelain;
3) 40 mg of amylase or amyloglucosidase;
4) 50 mg lactase; and
5) 45 mg of excipient.

Example G

A 250 mg Capsule or Tablet Containing 1) 75 mg of *C. cylindracea* lipase;
2) 20 mg of papain and 20 mg of bromelain;
3) 65 mg of amylase or amyloglucosidase;
4) 25 mg lactase; and
5) 45 mg of excipient.

Example H

A 250 mg Capsule or Tablet Containing 1) 100 mg of *C. cylindracea* lipase;
2) 30 mg of *R. niveus,* 30 mg of *A. niger,* 15 mg of bromelain, 15 mg of papain; and
3) 60 mg of excipient.

Example I

A 250 mg Capsule Containing 1) 75-100 mg of *Candida cylindracea* lipase;
2) 20-75 mg of protease;
3) 40-75 mg of amylase or amyloglucosidase;
4) 25-50 mg lactase; and
5) at least 45 mg of excipient.

Example J

A 250 mg Capsule Containing 1) about 15,000 FIP to about 20,000 FIP of *Candida cylindracea* lipase;
2) about 40 to about 75 AG of an amylase or amyloglucosidase;
3) about 36-72 SAPU of *Rhizopus niveus* protease, about 50-100 SAPU/g of *A. niger* and/or about 1,000-3,000 PU of bromelain, about 1,500-4,500 PU papain;
4) about 2,500 to about 5,000 ALU of lactase; and
5) excipient to 250 mg.

Example K

Activity Assays

One of skill in the art can determine enzyme activity for the enzymes contemplated by the present invention by using conventional assays known in the art. For example, enzyme activity can be determined by using the procedures provided in *Food Chemicals Codex*, Fifth Edition, Effective Jan. 1, 2004, Appendix V: Enzyme Assays. See e.g., "Lipase (Microbial) Activity for Medium- and Long-Chain Fatty Acids" (FIP); "Lactase (Acid) β-Galactosidase) Activity" (ALU); "Glucoamylase Activity (Amyloglucosidase Activity)" (AG); "Plant Proteolytic Activity" (PU); "Proteolytic Activity, Fungal (SAP)" (SAPU).

Example L

In Vivo Effectiveness of an Enzyme Mixture According to the Invention on Pigs Suffering from Pancreatic Insufficiency Tests are carried out on adult female Gottingen miniature pigs of the Ellegaard line (33-40 kg body weight), into each of which an ileocaecal bypass cannula is inserted. The bypass cannula serves to collect the chyme from the test animals. A group of these animals furthermore have the pancreatic duct ligated (=test animals). The other animals retain an intact pancreatic duct and serve as a control for the test results (=control animals). Tests can be performed with different doses of an enzyme mixture according to the invention.

Per dose, all the animals are fed, over a period of 22 days, twice daily with 250 g each time of a fat-rich test food containing 170 g husbandry feed for miniature pigs (Altromin®, from Lukas Meyer; substantially double-ground wheat), 10 g protein concentrate (Sojamin 90®, from Lukas Meyer), 70 g soya oil (from Roth) and 0.625 g $Cr_2O_3$ (as non-resorbable marker, from Roth), mixed with 1 liter of water. Additionally, the individual enzymes of the enzyme mixture according to the invention are admixed in the corresponding quantity to the feed of only the test animals shortly before feeding. Additionally, a series of tests are carried out with a subgroup of the test animals, in which no enzyme mixture is added to their test feed. The results obtained in this series of tests are given as "zero values." In each case on the 20th to 22nd days of the investigation period, chyme samples are taken from the bypass cannula of the test animals over a period of 12 hours, and these are investigated in terms of their content of crude fat, crude protein and starch. The feeding tests and their evaluation are carried out in known manner (cf. P. C. Gregory, R. Tabeling, J. Kamphues, "Biology of the Pancreas in Growing Animals"; Developments in Animal and Veterinary Sciences 28 (1999) 381-394, Elsevier, Amsterdam; editors: S. G. Pierzynowski and R. Zabielski).

It will be clear from test results that by administering an enzyme mixture according to the invention a significant improvement in the digestibility of fats, proteins and carbohydrates is achieved in pigs suffering from pancreatic insufficiency.

Example M

Human Example

A cohort of patients afflicted with cystic fibrosis and who show symptoms of pancreatic insufficiency are selected. Administer the composition of the invention to test patients at a time before, during and after ingestion of food. It will be clear from test results that by administering an enzyme mixture according to the invention within an hour of ingestion of the food, a significant improvement in the digestibility of fats, proteins and carbohydrates is achieved in patients suffering from pancreatic insufficiency.

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, pharmacology, microbiology and/or related fields are intended to be within the scope of the following claims.

All publications and patent applications mentioned in this specification are indicative of the level of skill of those skilled in the art to which this invention pertains. All such publications and patent applications are herein incorporated by reference to the same extent as if each individual publication or patent application was specifically and individually indicated to be incorporated by reference.

What is claimed is:

1. A method of treating pancreatic enzyme insufficiency comprising administering an effective amount of a composition comprising a *Candida cylindracea* lipase, at least one protease, and optionally an amylase and/or amyloglucosidase to a patient suffering from a pancreatic enzyme insufficiency, wherein said lipase exhibits at least 50% of its maximum activity at a pH of 2.0 to 8.0, wherein the lipase and the at least one protease are from different sources.

2. The method of claim 1, wherein the lipase retains at least 50% of its initial activity upon exposure to a pH of 2.0 to 7.0 for about 30 minutes.

3. The method of claim 1, wherein said composition comprises an amylase and/or amyloglucosidase.

4. The method of claim 3, wherein said amylase and/or amyloglucosidase is a fungal amylase and/or fungal amyloglucosidase.

5. The method of claim 4, wherein said fungal amylase and/or fungal amyloglucosidase is from *Rhizopus niveus*.

6. The method of claim 4, wherein said fungal amylase and/or fungal amyloglucosidase is from *A. oryzae*.

7. The method of claim 1, wherein said composition comprises at least one acid protease.

8. The method of claim 1, wherein said at least one protease is selected from the group consisting of papain protease, bromelain protease, microbial acid protease, *Aspergillus niger* protease, *Rhizopus niveus* protease and combinations thereof.

9. The method of claim 8, comprising two or more proteases which are from different sources.

10. The method of claim 9, comprising an acid protease and one of bromelain protease or papain protease.

11. The method of claim 10, wherein said acid protease is an *Rhizopus niveus* protease.

12. The method of claim 3, wherein said composition further comprises lactase.

13. The method of claim 1, wherein said patient suffers from cystic fibrosis.

14. The method of claim 1, wherein said composition comprises a *Candida cylindracea* lipase, at least one acid stable protease, and a fungal amylase and/or fungal amyloglucosidase.

15. The method of claim 13, wherein said composition comprises a *Candida cylindracea* lipase, at least one acid stable protease, and a fungal amylase and/or fungal amyloglucosidase.

16. The method of claim 14, wherein said at least one acid stable protease and said fungal amyloglucosidase is from *Rhizopus niveus*.

17. The method of claim 14, wherein said composition further comprises lactase.

18. A method of preparing an orally administered enzyme composition, comprising:

obtaining each of a lipase, at least one protease, and optionally an amylase and/or amyloglucosidase, wherein said lipase is exhibits at least 50% of its maximum activity at a pH of 2.0 to 8.0, wherein the lipase and the at least one protease are from different sources and combining said lipase, said at least one protease, and optionally said amylase and/or amyloglucosidase to form the orally administered enzyme composition, wherein said composition comprises one or more dosage units having an effective amount of said lipase and said at least one protease.

19. The method of claim 18, further comprising obtaining an amylase and/or amyloglucosidase and combining said amylase and/or amyloglucosidase with said lipase and said at least one protease.

20. The method of claim 19, wherein said amylase and/or amyloglucosidase is a fungal amylase and/or fungal amyloglucosidase.

21. The method of claim 18, wherein said at least one protease is an acid protease.

22. The method of claim 19, further comprising obtaining lactase and combining said lactase with said lipase, said at least one protease, and said amylase and/or amyloglucosidase.

* * * * *